US00PP24505P3

(12) United States Plant Patent
Korlipara

(10) Patent No.: US PP24,505 P3
(45) Date of Patent: May 27, 2014

(54) *ECHINACEA* PLANT NAMED 'CHIQUITA'

(50) Latin Name: ***Echinacea* hybrid**
Varietal Denomination: Chiquita

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 87 days.

(21) Appl. No.: 13/573,340

(22) Filed: Sep. 11, 2012

(65) Prior Publication Data

US 2014/0075632 P1 Mar. 13, 2014

(51) Int. Cl.
*A01H 5/00* (2006.01)

(52) U.S. Cl.
USPC ..... Plt./428

(58) Field of Classification Search
USPC ..... Plt./428
See application file for complete search history.

*Primary Examiner* — Annette Para
(74) *Attorney, Agent, or Firm* — Klarquist Sparkman, LLP

(57) ABSTRACT

A new and distinct *Echinacea* plant named 'Chiquita' characterized by light yellow ray florets, numerous, 10 cm wide inflorescences, a well branched, upright, dwarf habit, and excellent vigor.

1 Drawing Sheet

Botanical denomination: *Echinacea* hybrid.
Variety designation: 'Chiquita'.

BACKGROUND OF THE INVENTION

The present invention relates to a new and distinct cultivar of *Echinacea* and given the cultivar name 'Chiquita'. *Echinacea* is in the family Asteraceae. This new cultivar is part of a planned breeding program to develop dwarf *Echinacea* hybrids. This cultivar was selected for its compact free flowering habit with light pink inflorescences. The exact parents of this selection are unknown, unnamed, proprietary interspecific hybrid plants.

Compared to *Echinacea* 'Amber Mist' (U.S. Pat. No. 21,811), the new cultivar has larger inflorescences and light yellow ray florets rather than yellow orange.

This new *Echinacea* cultivar is distinguished by:

1. light yellow ray florets,
2. numerous, 10 cm wide inflorescences,
3. a well branched, upright, dwarf habit, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows *Echinacea* 'Chiquita' in bloom on a one-year-old plant growing in the garden in full sun in late July in Canby, Oreg.

DETAILED PLANT DESCRIPTION

The following is a detailed description of the new *Echinacea* cultivar based on observations of 18-month-old specimens growing in the garden in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in Canby, Oreg. The color descriptions are all based on The *Royal Horticultural Society Colour Chart,* 5$^{th}$ edition.

Plant:

*Type.*—Herbaceous perennial.
*Hardiness.*—USDA Zones 4 to 9.
*Size.*—Grows to about 28 cm wide and 43 cm tall to top of inflorescences.
*Form.*—Basal clump, with about 8 stems from the base.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 1 to 3 inflorescences per stem.
*Size.*—To 39 cm tall to a terminal inflorescence and 6 mm wide at base.
*Internode length.*—2 cm to 6 cm.
*Surface texture.*—Strigose.
*Color.*—Yellow Green 146B.

Leaf:

*Type.*—Simple.
*Shape.*—Ovate to lanceolate.
*Arrangement.*—Basal.
*Blade size.*—Grows to 13 cm long and 5.5 cm wide.
*Margins.*—Entire, slightly undulate.
*Apex.*—Acuminate.
*Base.*—Attenuate.
*Surface texture.*—Strigose on both sides.
*Venation.*—Pinnate, with 3 main veins, veins Yellow Green 149D on top side and 146D on bottom.
*Color.*—Topside Green 137A bottom side closest to Yellow Green 147B.
*Petiole description.*—Grows to 4.5 cm long and 5 mm wide, strigose on top edges, glabrous on bottom, Yellow Green 146D on bottom side and top side base, leafy edges on topside 137A.

Inflorescence:

*Type.*—Composite on terminal stalked heads.

*Number of flowering stems from the ground.*—About 8.

*Flowering stem.*—Grows to 39 cm tall from the base of the plant to the terminal inflorescence and can grow to 10 cm long from the top stem leaf to the base of an inflorescence; branched with 1 to 3 inflorescences per stem; diameter growing to 7 mm wide near the inflorescence; strigose; Yellow Green 146B.

*Size.*—Grows to 10.5 cm wide and 4.5 cm deep as disc enlarges.

*Form.*—Ray florets held mostly horizontally, mature disc is conic.

*Immature inflorescence.*—Grows to 2.5 cm wide and 2.5 cm deep, ray florets held at an angle (about 40 degrees from horizontal) and rolled up so only the back color shows, Yellow 8D, disc color Yellow Green 146A.

*Ray florets.*—Without pistil or stamen, to 27 in number, grow to 45 mm long and 12 mm wide, sometimes quilled at base, usually oblanceolate with the tip 2-toothed and acute, entire margins, base attenuate, glabrous on both sides; topside Yellow 11B, bottom side closest to 8D.

*Disc.*—Flat becoming conic, becoming 22 mm deep and 40 mm wide with maturity, Yellow Green 146A in background with prominent bracts Orange 23A overall.

*Disc florets.*—About 350 in number, each with 1 pistil and 4 stamen, grow to 12 mm long and 1.5 mm wide, each with one persistent, very stiff linear bract (15 mm long with the top 3 mm Orange 23A, then 5 mm Yellow Green 144A blending to White 155A at base); corollas 5 mm long and 1 mm wide, tubular, 5 lobed, glabrous inside and out, Greyed Yellow 160C with top and bottom Yellow Green 146D; pistil 12 mm long, ovary 3.5 mm long, White NN155D, style 7 mm long Yellow Green 145C, 2-branched stigma spreading, Yellow Green N144A; stamen 6 mm long, filaments 3 mm long and White 155A, anthers 3 mm long and Greyed Purple N186A, pollen Yellow Orange 16A.

*Phyllaries.*—In 4 leafy series, area grows to 30 mm wide and 17 mm deep, lobes lanceolate in shape, reflexed, grow to 12 mm long and 3.7 mm wide, Yellow Green 147B, margins strigose, tip acute, strigose on both sides.

*Receptacle.*—Grows to 12 mm wide and 10 mm deep, White 155B.

*Bloom period.*—July through October in Canby, Oreg.

*Fragrance.*—Floral, sweet.

*Lastingness.*—Each inflorescence lasts about two weeks in Canby, Oreg.

Seeds: 3 mm long and 2.5 mm wide, oval, Brown 200C.

*Fertility.*—Good.

Disease and pests: No pests or diseases have been observed on plants grown under commercial conditions in Canby, Oreg. No resistances are known.

I claim:

1. A new and distinct *Echinacea* plant as herein illustrated and described.

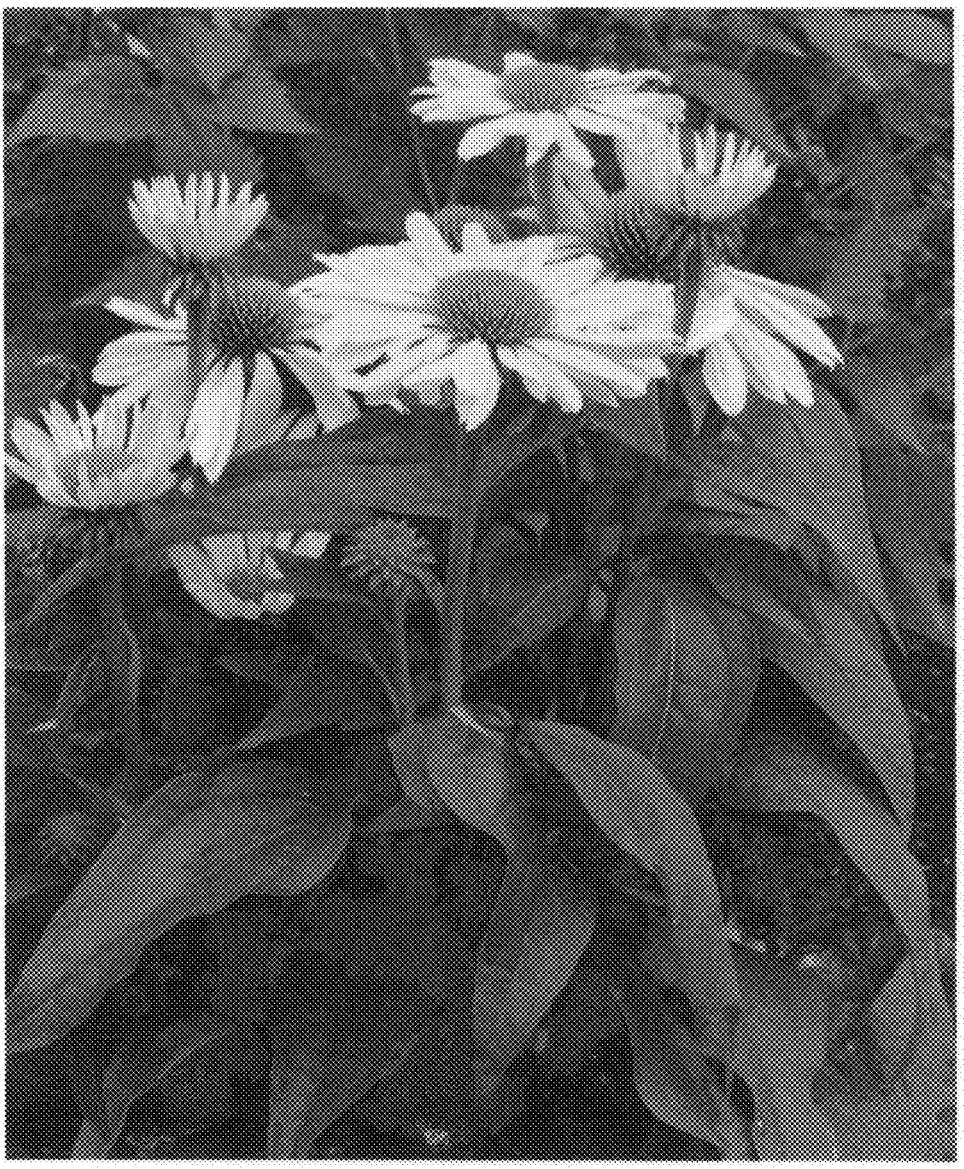

* * * * *